(12) United States Patent
Asano et al.

(10) Patent No.: US 8,046,043 B2
(45) Date of Patent: Oct. 25, 2011

(54) EXTRACTION DEVICE, ANALYZER, EXTRACTION METHOD, AND ANALYSIS METHOD

(75) Inventors: Kaoru Asano, Kobe (JP); Yasunori Maekawa, Kobe (JP); Seiki Okada, Kobe (JP)

(73) Assignee: Sysmex Corporation, Kobe (JP)

( * ) Notice: Subject to any disclaimer, the term of this patent is extended or adjusted under 35 U.S.C. 154(b) by 718 days.

(21) Appl. No.: 11/280,100

(22) Filed: Nov. 16, 2005

(65) Prior Publication Data

US 2006/0116563 A1 Jun. 1, 2006

(30) Foreign Application Priority Data

Nov. 16, 2004 (JP) ................................. 2004-331669
Mar. 31, 2005 (JP) ................................. 2005-100346

(51) Int. Cl.
*A61B 5/05* (2006.01)
*A61B 5/00* (2006.01)

(52) U.S. Cl. .......................... 600/347; 600/345; 600/365

(58) Field of Classification Search .................. 600/345, 600/347, 365; 604/20; 422/50, 420–424
See application file for complete search history.

(56) References Cited

U.S. PATENT DOCUMENTS

| | | | | |
|---|---|---|---|---|
| 5,037,381 A | * | 8/1991 | Bock et al. | 604/20 |
| 5,279,543 A | | 1/1994 | Glikfeld et al. | |
| 5,722,397 A | * | 3/1998 | Eppstein | 600/345 |
| 5,827,183 A | | 10/1998 | Kurnik et al. | |
| 6,201,979 B1 | * | 3/2001 | Kurnik et al. | 600/345 |
| 6,587,705 B1 | | 7/2003 | Kim et al. | |
| 7,228,163 B2 | * | 6/2007 | Ackerman | 600/347 |
| 7,295,867 B2 | * | 11/2007 | Berner et al. | 600/345 |
| 2002/0019604 A1 | | 2/2002 | Tierney | |
| 2003/0100846 A1 | | 5/2003 | Custer et al. | |
| 2003/0199745 A1 | * | 10/2003 | Burson et al. | 600/347 |
| 2004/0132167 A1 | | 7/2004 | Rule et al. | |
| 2004/0193219 A1 | * | 9/2004 | Asano et al. | 607/1 |
| 2004/0220495 A1 | | 11/2004 | Cahir et al. | |
| 2005/0096520 A1 | * | 5/2005 | Maekawa et al. | 600/365 |
| 2006/0058602 A1 | * | 3/2006 | Kwiatkowski et al. | 600/407 |

FOREIGN PATENT DOCUMENTS

| | | |
|---|---|---|
| EP | 0987333 | 3/2000 |
| JP | 2004-159994 A | 6/2004 |
| WO | WO 96/00110 A1 | 1/1996 |
| WO | WO 01/70330 A2 | 9/2001 |

OTHER PUBLICATIONS

European Search Report for Application No. 07012591.9 dated Sep. 20, 2007.

* cited by examiner

*Primary Examiner* — Patricia Mallari
*Assistant Examiner* — Christian Jang
(74) *Attorney, Agent, or Firm* — Brinks Hofer Gilson & Lione

(57) ABSTRACT

An extraction device for extracting an analyte from living tissue is disclosed that comprises a power source; a first electrode and second electrode connected to the power source; and a holding unit for holding a collecting medium for collecting analyte extracted from living tissue, wherein the collecting medium is in contact with both the first electrode and second electrode continuously. An analyzer comprising the extraction device, method for extracting an analyte, and method for extracting and analyzing an analyte are also described.

4 Claims, 12 Drawing Sheets

EXTRACTION DEVICE, ANALYZER, EXTRACTION METHOD, AND ANALYSIS METHOD

This application claims priority under 35 U.S.C. §119 to Japanese Patent Application Nos. 2004-331669 filed Nov. 16, 2004 and 2005-100346 filed Mar. 31, 2005, the entire contents of which are hereby incorporated by reference.

TECHNICAL FIELD

The present invention relates to an extraction device, analyzer, extraction method, and analysis method, and specifically relates to an extraction device for extracting analyte from living tissue, analyzer, extraction method, and analysis method.

BACKGROUND

Conventional clinical examinations are generally performed by detecting the presence and measuring the amount of material in a collected blood specimen. For example, diabetes patients, themselves, frequently-measure their blood sugar level and determine the insulin dosage and food restrictions and amount of exercise based on the measured blood sugar level, as they self-manage their blood sugar. In this way the diabetes patient must measure her blood sugar level several times per day. Since measuring the blood sugar level is normally accomplished by measuring a blood sample collected using a piercing tool, there is some associated physical pain and stress for the patient. From this point of view, a simple examination that is less stressful for the patient and that does not require blood collection is very desirable.

In response to this desire, conventional devices have been disclosed that use a so-called reverse iontophoresis to extract interstitial fluid by means of an electrical current flowing through the skin (for example, U.S. Pat. No. 5,279,543, and International Patent Publication No. 96/00110). In the devices using the reverse iontophoresis method disclosed in these patent publications, interstitial fluid is extracted using two collection media corresponding to a positive electrode and negative electrode.

In the devices using the reverse iontophoresis method disclosed in these patent publications, since interstitial fluid is extracted using two collection media corresponding to a positive electrode and negative electrode, the analyte extracted from living tissue is dispersed in the two collection media. Therefore, a problem arises with regard to the pain and damage to the subject because a relatively large electric current is required to extract to the two collection media the amount of analyte necessary for analysis within a predetermined time.

SUMMARY

The scope of the present invention is defined solely by the appended claims, and is not affected to any degree by the statements within this summary. An object of the present invention is to eliminate the aforesaid problem by providing an extraction device and extraction method capable of extracting from a subject an amount of analyte necessary for analysis within a predetermined time and without undue discomfort to the subject by efficiently collecting analyte.

A first aspect of the present invention relates to an extraction device for extracting an analyte from living tissue, the device comprising: a power source; a first electrode and second electrode connected to the power source; and a holding unit for holding a collecting medium for collecting analyte extracted from living tissue, wherein the collecting medium is in contact with both the first electrode and second electrode continuously.

A second aspect of the present invention relates to a method for extracting an analyte from living tissue, the method comprising of the steps of: bringing a collection medium for collecting analyte extracted from living tissue into contact with the skin, wherein the collection medium is in contact with both a first electrode and a second electrode continuously; and extracting analyte from the living tissue to the collection medium by applying a voltage between the first electrode and second electrode.

A third aspect of the present invention relates to a device for extracting an analyte from living tissue, the device comprising: an electric field inducing means for providing an electric field in living tissue through a nonconductive material; and a collection medium for collecting an analyte extracted from living tissue in the presence of an electric field induced by the electric field inducing means.

DETAILED DESCRIPTION

Preferred embodiments of the present invention are described hereinafter.

Figure 1:
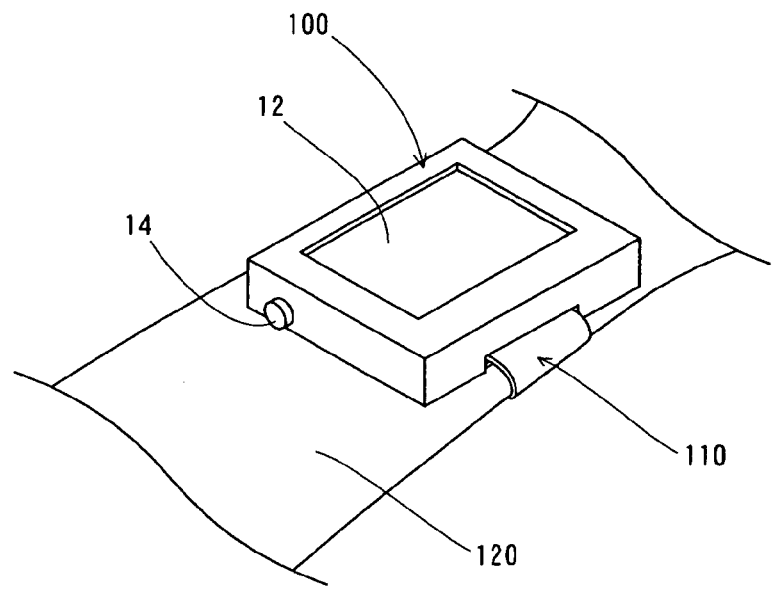
FIG. 1 is a perspective view of a blood sugar measuring device of an embodiment of the present invention installed on the wrist of a subject.
Figure 6:
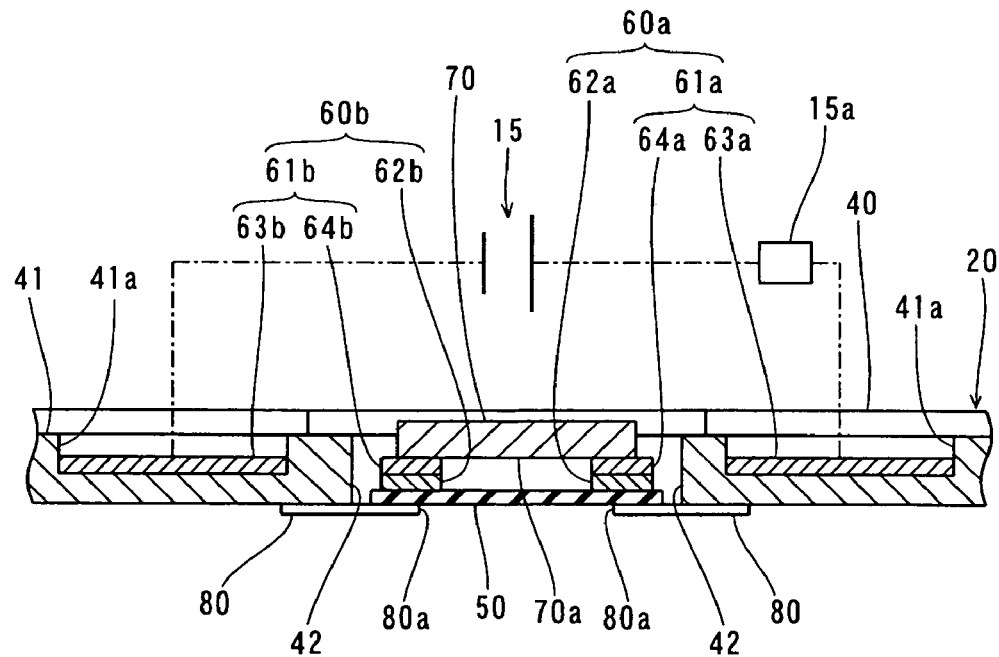
FIG. 6 is an enlargement showing the embodiment of the blood sugar measuring device of FIG. 5 mounted on the wrist of a subject.
Figure 7:
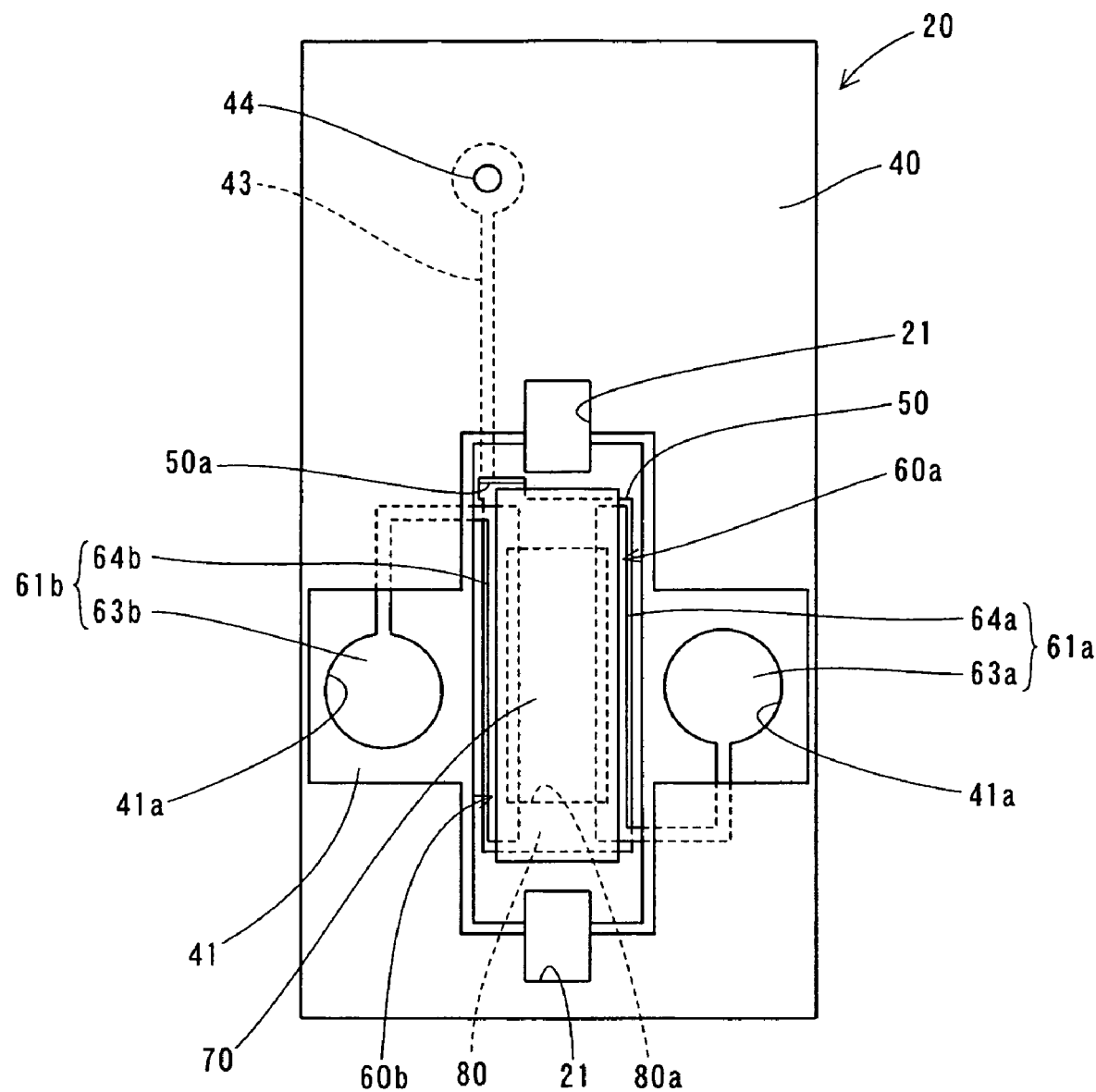
FIG. 7 is a top view showing the structure of the extraction cartridge of the embodiment of the blood sugar measuring device of FIG. 2.
Figure 8:
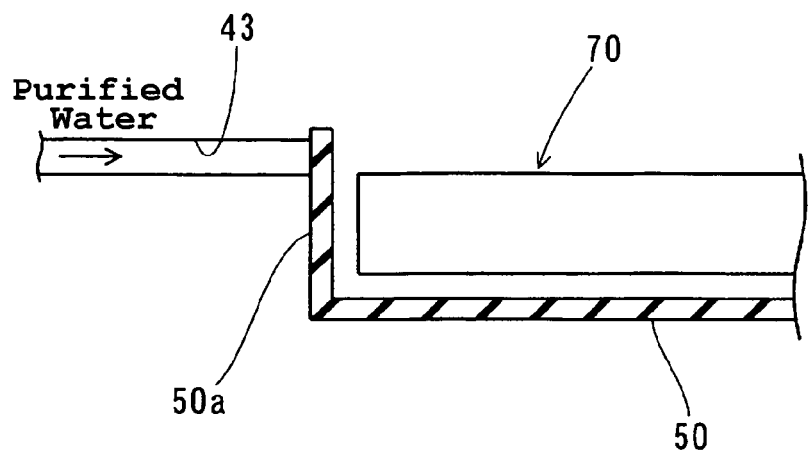
FIG. 8 shows a contact part of a paper sheet and purified water supply path in the extraction cartridge of the embodiment of the blood sugar measuring device of FIG. 7.
Figure 9:
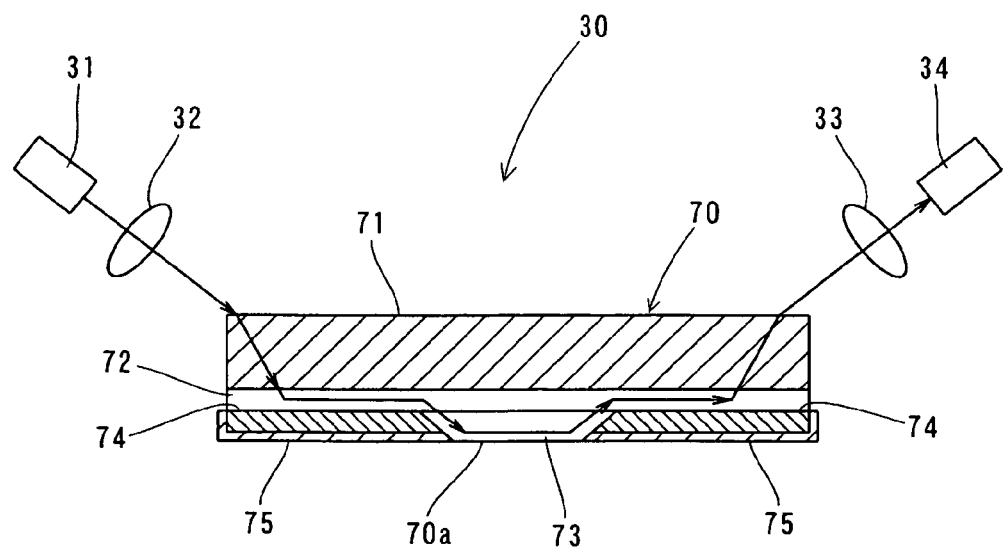
FIG. 9 briefly shows the structure of the detecting unit of the embodiment of the blood sugar measuring device of FIG. 1.
Figure 10:
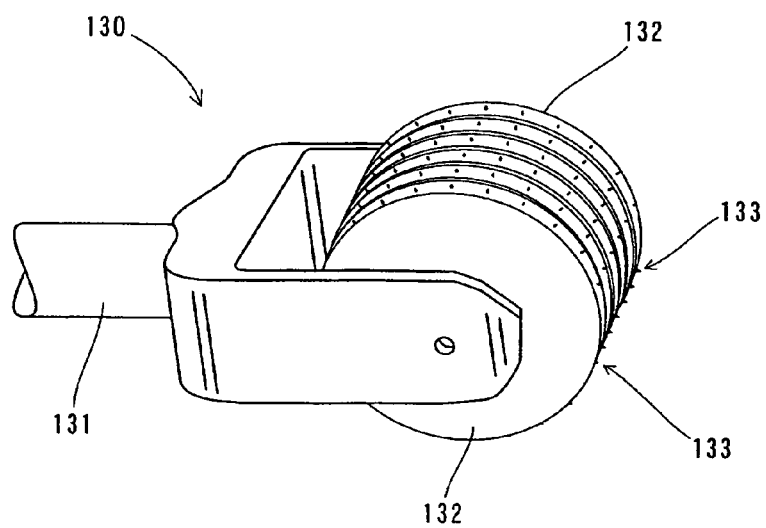
FIG. 10 is a perspective view of the micro needles used in preprocessing.
Figure 11:
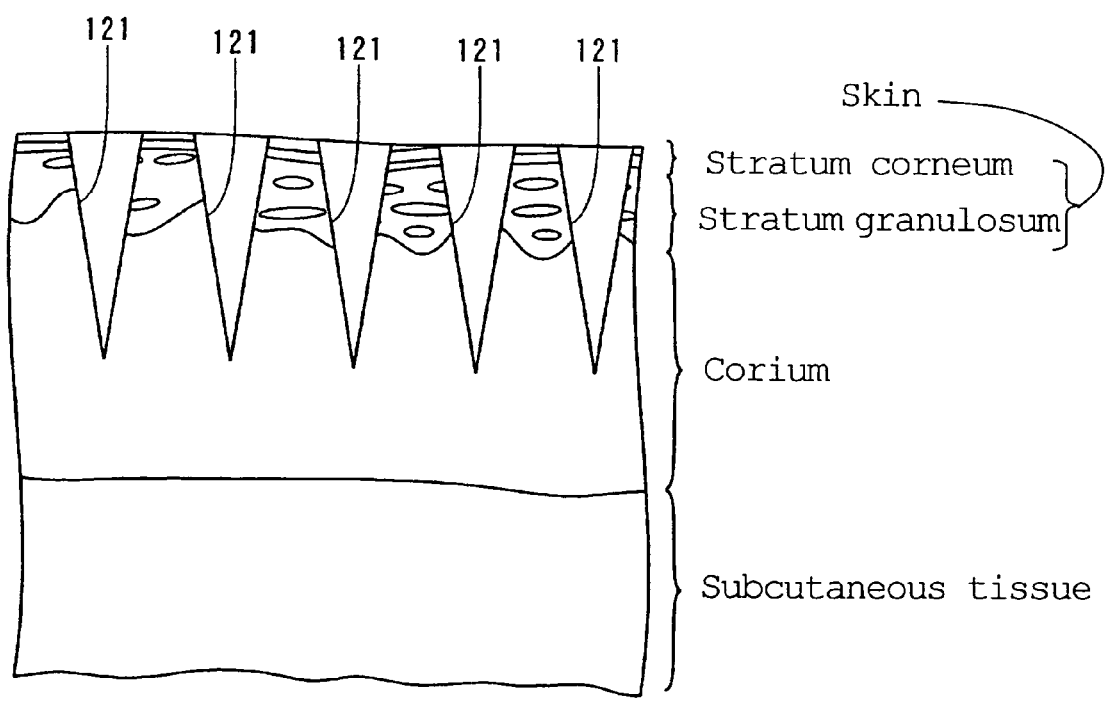
FIG. 11 is a section view showing a state of the skin preprocessed by using the micro needles of FIG. 10.

FIG. 1 is a perspective view of a blood sugar measuring device of an embodiment of the present invention installed on the wrist of a subject. FIGS. 2 through 5 are top views showing the internal structure of the blood sugar measuring device of the embodiment of FIG. 1. FIG. 6 is a section view corresponding to FIG. 5 of a blood sugar measuring device of an embodiment of the present invention installed on the wrist of a subject. FIG. 7 is a top view showing the structure of the extraction cartridge of the embodiment of the blood sugar measuring device of FIG. 2. FIG. 8 shows a contact part of a paper sheet and purified water supply path in the extraction cartridge of the embodiment of the blood sugar measuring device of FIG. 7. FIG. 9 briefly shows the structure of the detecting unit of the embodiment of the blood sugar measuring device of FIG. 1. FIG. 10 is a perspective view of the micro needles used in preprocessing; FIG. 11 is a section view showing a state of the skin preprocessed by using the micro needles of FIG. 10. The overall structure of an embodiment of the blood sugar measuring device 100 of the present invention is described below with reference to FIGS. 1 through 11.

The embodiment of the blood sugar measuring device 100 of the present invention extracts interstitial fluid containing glucose as one biochemical component from living tissue, and calculates the blood sugar level by analyzing the glucose contained in the extracted interstitial fluid. The blood sugar measuring device 100 is configured so as to be mountable on the wrist 120 of a subject using a band 110. The band 110 has openings at predetermined positions, such that the blood sugar measuring device 100 can be mounted by an anchoring fixture (not shown in the drawing) to anchor the blood sugar measuring device 100. The subject attaches the band 110 to the wrist 120 without the blood sugar measuring device mounted, performs preprocessing of the extraction area of the wrist 120 through the anchoring fixture opening using a needle roller 130 (refer to FIG. 10), and thereafter mounts the blood sugar measuring device 100 to the anchoring fixture.

The needle roller 130 is configured by an arm 131, and a plurality of rollers 132 rotatably supported on the arm 131, as shown in FIG. 10. On the exterior surface of the roller 132 are formed a plurality of small needles 133 at equally spaced intervals. The needles 133 have a penetration depth (approximately 0.3 mm) sufficient to pass through the skin including the stratum corneum, but not to attain the subcutaneous tissue when pressed against the skin. As shown in FIG. 11, the surface of the skin is penetrated to the corium, and small extraction holes 121 that do not reach to the subcutaneous tissue are formed by the preprocessing using the needle roller 130, that is, the process of pressing the needles 133 against the extraction area. In the present embodiment, interstitial fluid containing glucose is easily extracted from living tissue through the plurality of extraction holes 121 by forming the extraction holes 121. Accordingly, there is little sensation of discomfort to the subject when glucose is extracted from living tissue using the blood sugar measuring device 100. In the present embodiment, a derma roller manufactured by Top-Rol Corporation is used as the needle roller 130.

Figure 2:
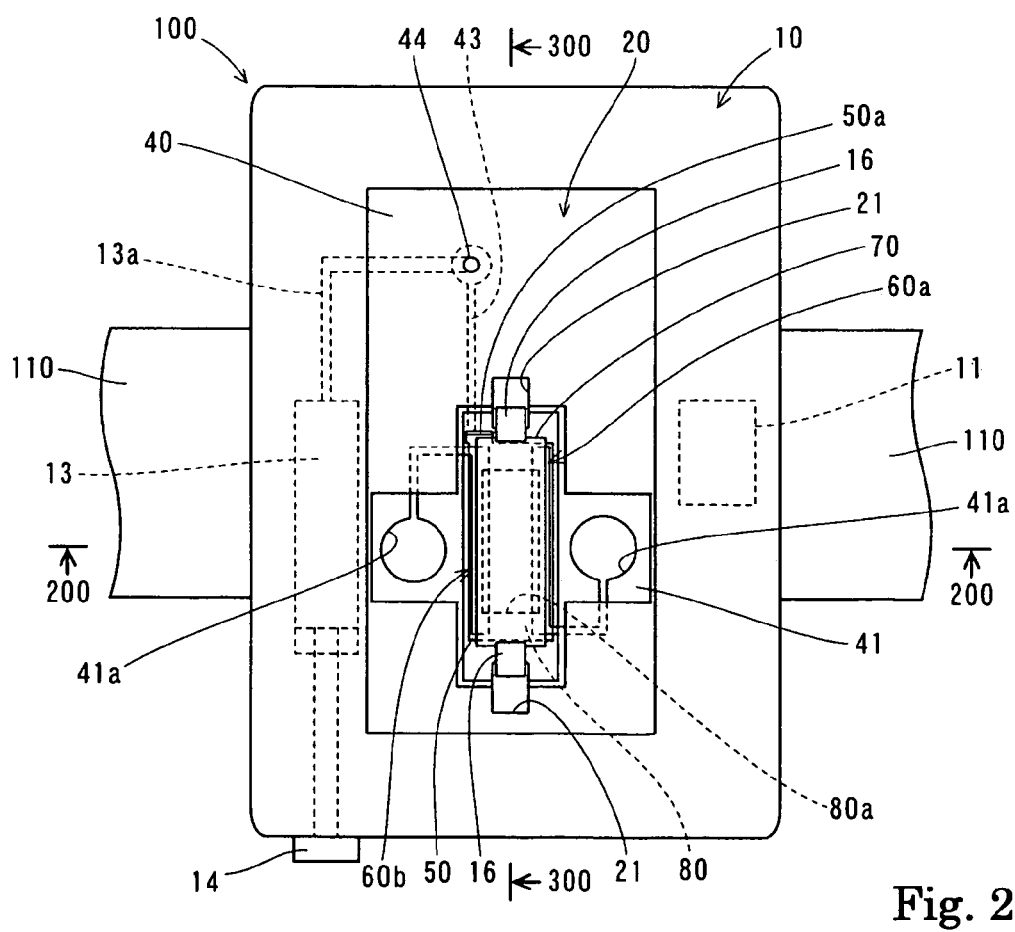
FIG. 2 is a top view showing the internal structure of the embodiment of the blood sugar measuring device of FIG. 1.
Figure 3:
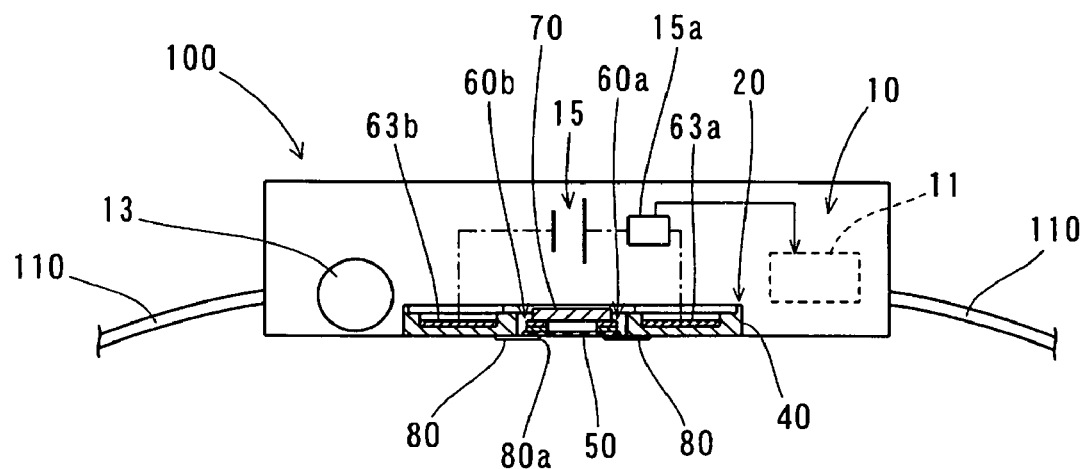
FIG. 3 is a section view along the 200-200 line in FIG. 2.

As shown in FIGS. 2 and 3, the blood sugar measuring device 100 is provided with an analysis unit 10 as a device body, and an extraction cartridge 20 which is detachably installed in the analysis unit 10. The analysis unit 10 includes a control unit 11, display unit 12 (refer to FIG. 1), syringe 13, measurement start switch 14, direct current constant voltage power source 15, ammeter 15a for measuring the current from the constant voltage power source 15 and outputting the measurement result to the control unit 11 and two connecting hooks 16. The analysis unit 10 is further provided with a monochrome light source 31, lens 32, lens 33, and photoreceptor element 34, which configure the detecting unit 30 shown in FIG. 9. The photoreceptor 34 outputs a signal based on the amount of received light.

The control unit 11 calculates the glucose extraction rate (amount extracted per unit time) based on the signal output from the photoreceptor element 34 (refer to FIG. 9), and calculates the blood sugar level based on the average value (average extraction current value) of the magnitude of the current flowing from the constant voltage power source 15 during glucose extraction and the calculated glucose extraction rate. The display unit 12 (refer to FIG. 1) is provided to display the blood sugar level and glucose extraction rate calculated by the control unit 11.

The syringe 13 is provided to accommodate purified water as a collection medium for glucose, and to supply purified water to the extraction cartridge 20. As shown in FIG. 2, a tube 13a is provided on the syringe 13 to connect the syringe 13 with the extraction cartridge 20. The measurement starting switch 14 is connected to the syringe 13. In the blood sugar measuring device 100 of the present embodiment, the syringe 13 is actuated by pressing the measurement starting switch 14, such that the purified water within the syringe 13 is supplied to the extraction cartridge 20. The purified water used in the present embodiment has an electrical resistivity (specific resistance) of 18.3 MΩ·cm, and is substantially an insulating body (nonconductive material).

Figure 4:
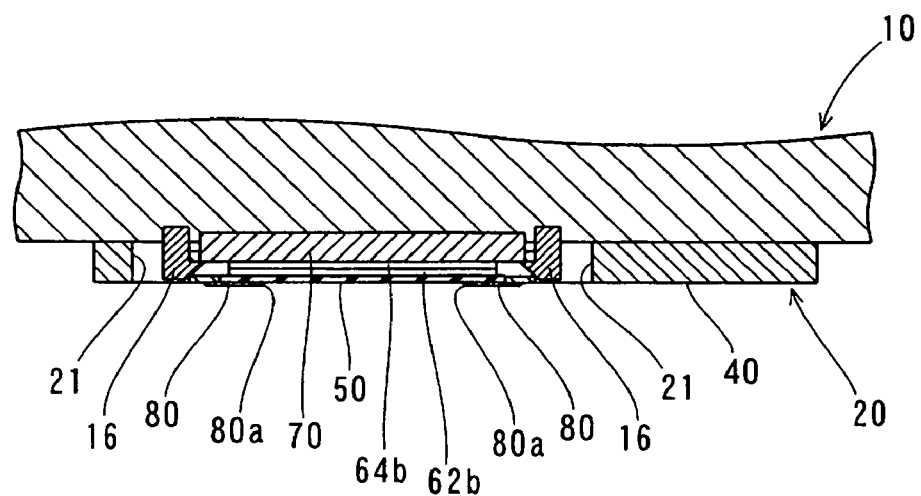
FIG. 4 is a section view along the 300-300 line in FIG. 2.
Figure 5:
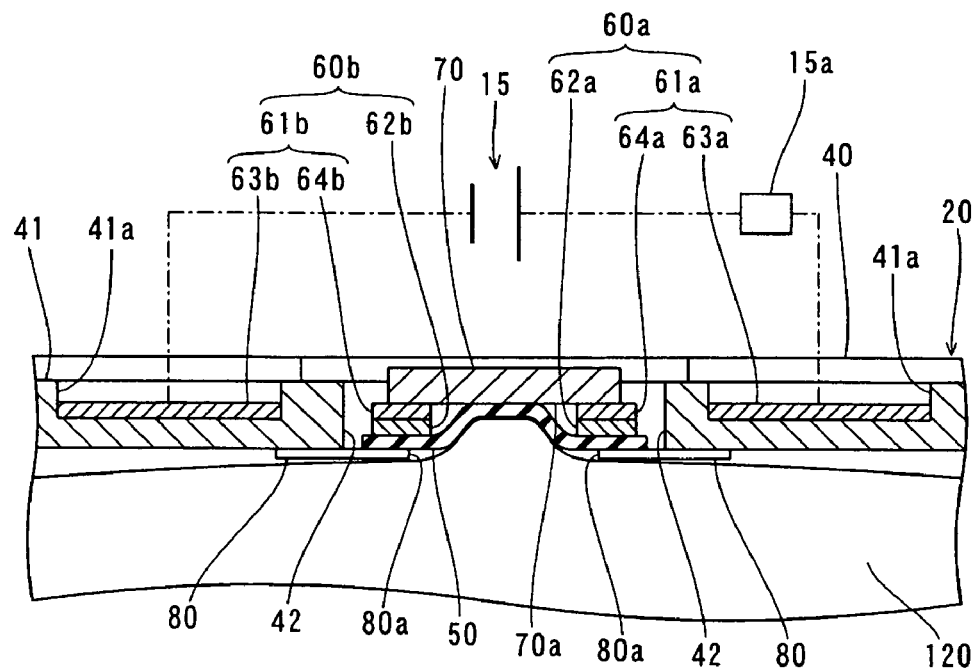
FIG. 5 is a partial enlargement of the embodiment of the blood sugar measuring device of FIG. 3.

The constant voltage power source 15 is connected to the terminal 63a of the positive electrode 60a and the terminal 63b of the negative electrode 60b of the extraction cartridge 20, as shown in FIGS. 3 and 5. A voltage from the constant voltage power source 15 is applied between the positive electrode 60a and negative electrode 60b to induce an electric field in the skin of the subject. Furthermore, the two connecting hooks 16 are provided to anchor the detachable extraction cartridge 20 to the analysis unit 10, as shown in FIGS. 2 and 4. In addition, the monochrome light source 31 in the detection unit 30 provided in the analysis unit 10 functions to irradiate a sensor 70 described later with analysis light through the lens 32, as shown in FIG. 9. The light from the monochrome light source 31 irradiating the sensor 70 through the lens 32 passes through a predetermined pathway within the sensor 70 and impinges the photoreceptor element 34.

The extraction cartridge 20 is detachably anchored to the analysis unit 10 when the connection hooks 16 of the analysis unit 10 respectively engage the two mounting holes 21 formed in the extraction cartridge 20, as shown in FIGS. 2 and 4. The extraction cartridge 20 is configured so as to be replaced after each glucose measurement.

In the present embodiment, the extraction cartridge 20 includes an acrylic resin cartridge body 40, one sheet of paper 50 that absorbs and holds purified water so as to function as an absorbing member, positive electrode 60a and negative electrode 60b, sensor 70 configuring the detection unit 30 (refer to FIG. 9), and two-sided tape 80, as shown in FIGS. 5 and 7. A step unit 41 configured as a cross-shaped concavity is provided in the cartridge body 40, as shown in FIG. 7. In the center of the step unit 41 is formed a main opening 42 that reaches the bottom of the cartridge body 40, as shown in FIG. 5. Furthermore, concavities 41a are formed at positions interposing the main opening 42 of the step unit 41 therebetween. The terminals 83a and 63b of the positive electrode 60a and negative electrode 60b described later fit in the two concavities 41a. The paper sheet 50, sensor 70, action units 64a and 64b described later, and activated carbon electrodes 62a and 62b are maintained within the main body opening 42.

A purified water supply path 43 extending from inside the main body opening 42 along the cartridge body 40 in the length direction is provided in the cartridge body 40, as shown in FIG. 7. The purified water supply path 43 is connected to the syringe 13 of the analysis unit 10 through the tube 13a of the analysis unit 10 and a communicating hole 44 provided at the end of the purified water supply path 43, as shown in FIG. 2.

In the present embodiment, the single paper sheet 50 contacts the bottom surface of the activated carbon electrodes 62a and 62b described later, as shown in FIG. 5. The paper sheet 50 is fixedly attached from the bottom side of the cartridge body 40 by means of the two-sided tape 80, which has a thickness of approximately 0.15 mm. The two-sided tape 80 has an opening 80a for regulating the skin measurement location (extraction area). The paper sheet 50 has a connecting portion 50a that connects to the end of the purified water supply path 43 of the cartridge body 40, as shown in FIG. 7. The connecting portion 50a of the paper sheet 50 is bent in an L-shape, and purified water is supplied from the purified water supply path 43 to the perpendicular part of the connector 50a of the paper sheet 50. The purified water supplied to the connecting portion 50a of the paper sheet 50 permeates the entirety of the paper sheet 50 within a short time by means of capillary action. The paper sheet 50 is maintained in a dry state before measurement, and is positioned within the main body opening 42 so as to not come into contact with the sensor 70, as shown in FIG. 5. The paper sheet 50 contains the purified water supplied from the syringe 13 (refer to FIG. 2) during measurement. In this way the purified water is absorbed by the paper sheet 50 and is maintained within the main body opening 42. The paper sheet 50 is constructed so as to touch the bottom surface of the sensor 70 when raised upward from the skin of the wrist 120 of the subject through the opening 80a of the two-sided tape 80 during measurement, as shown in FIG. 6. The paper sheet 50 used in the present embodiment has a thickness of approximately 0.15 mm, and has a content of 60% polypropylene and 40% rayon. Therefore, the distance from the skin of the wrist 120 of the subject to the bottom surface of the sensor 70 during measurement matches the thickness of the paper sheet 50, and is approximately 0.15 mm in the present embodiment. Furthermore, the amount of purified water supplied from the syringe 13 to the paper sheet 50 is approximately 10 μl. The positive electrode 60a and negative electrode 60b are configured by activated carbon electrodes 62a and 62b formed of activated carbon as a porous conductive material, and collector electrodes 61a and 61b formed of aluminum, as shown in FIGS. 5 and 7. The collector electrodes 61a and 61b are configured by round-shaped ends 63a and 63b that fit into the two concavities 41a formed in the step unit 41 of the cartridge body 40, and action parts 64a and 64b that are connected to the ends 63a and 63b. The activated carbon electrodes 62a and 62b are adhered under the action parts 64a and 64b of the collector electrodes 61a and 61b, and have a specific surface area of approximately 1000 $m^2$/g to approximately 3000 $m^2$/g. The end 63a of the positive electrode 60a and the end 63b of the negative electrode 60b are connected to the direct current type constant voltage power source 15 of the analysis unit 15.

The sensor 70 is disposed above the action part 64a of the positive electrode 60a and the action part 64b of the negative electrode 60b, as shown in FIG. 5. The bottom side of the sensor 70 has a measuring surface 70a. An enzyme (glucose oxidase) acting as a catalyst for glucose, an enzyme (peroxidase) acting as a catalyst for hydrogen peroxide ($H_2O_2$), and a color-producing agent that produces a color in reaction with activated oxygen are applied to the measuring surface 70a. Examples of useful color-producing agents include N,N-bis (2-hydroxy-3-sulfopropyl)tolidene dipotassium salt, and 3,3',5,5'-tetramethylbenzylidene and the like. The sensor 70 is configured by a glass substrate 71, first optical waveguide layer 72 mounted below the substrate 71, second optical waveguide layer 73 mounted in the center below the first optical waveguide 72, protective layer 74 formed below the first optical waveguide layer 72 so as to have the second optical waveguide layer 73 interposed therebetween, and a shield layer 75 covering the exterior side of the protective layer 74, as shown in FIG. 9. The first optical waveguide layer 72 has a refractive index higher than the substrate 71. The second optical waveguide layer 73 has a refractive index higher than the first optical waveguide layer 72, and has a laterally inclined trapezoidal shape. The measuring surface 70a of the sensor 70 is exposed from the protective layer 74 after the second optical waveguide layer 73, and contacts the top surface of the paper sheet 50 during measurement as shown in FIG. 6. The detection unit 30 of the present embodiment is configured by the sensor 70, and monochrome light source 31, lens 32, lens 33, and photoreceptor element 34 of the analysis unit 10 described above.

Figure 12:
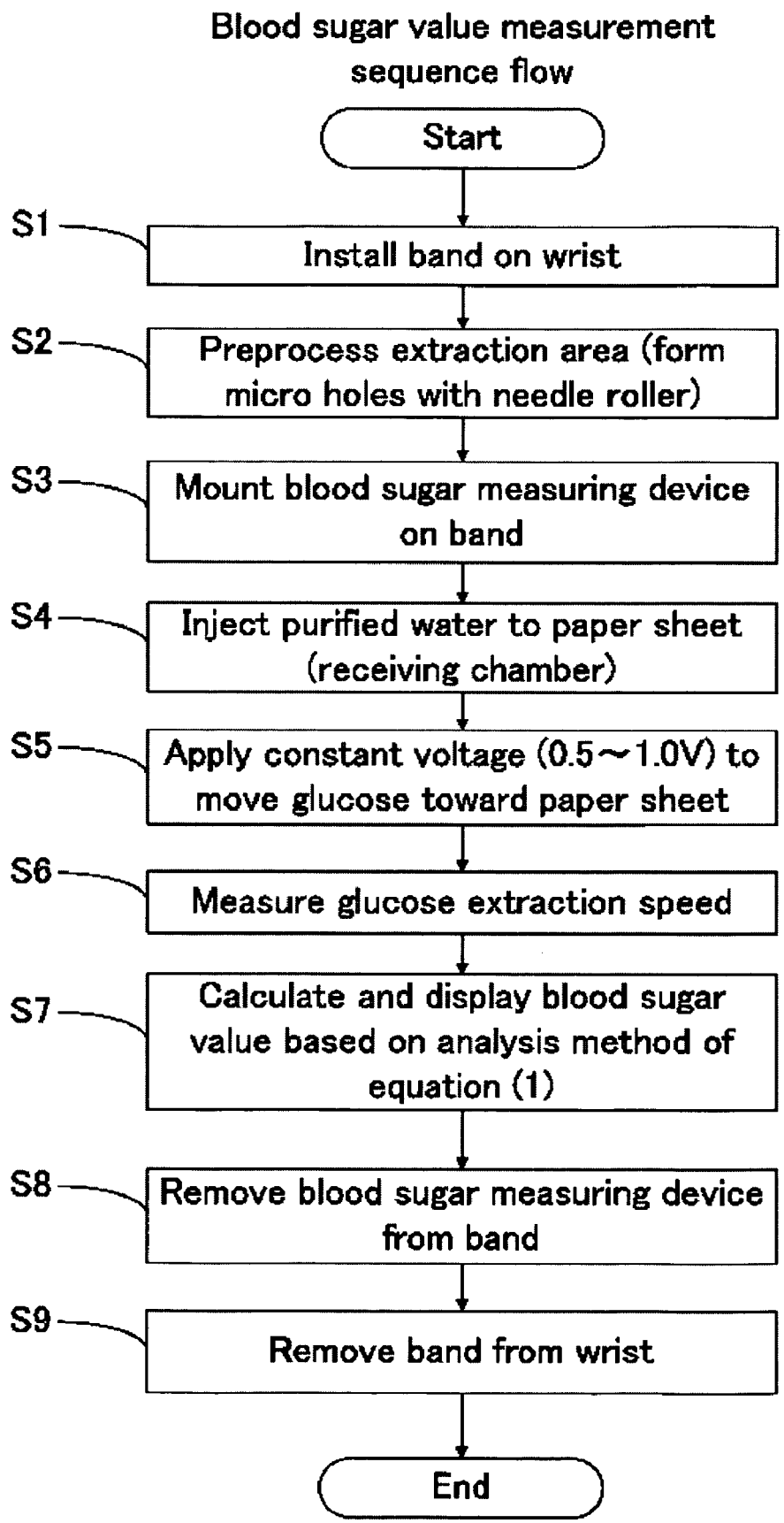
FIG. 12 is a flow chart showing the sequence of the blood sugar measuring operation used in the embodiment of the blood sugar measuring device of FIG. 1.
Figure 17:
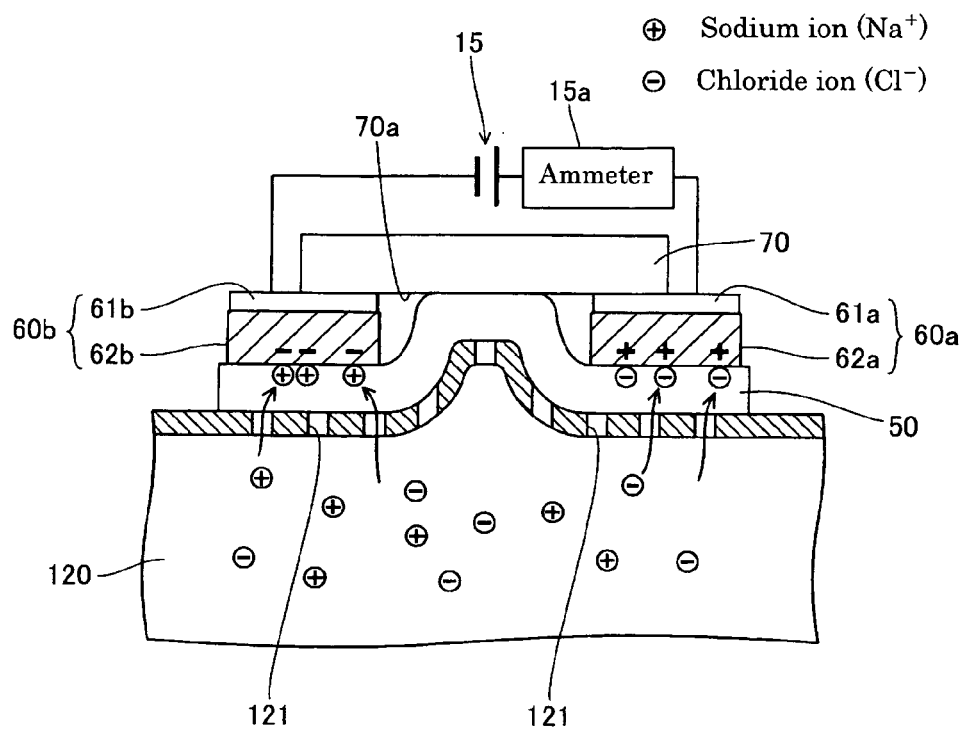
FIG. 17 is a schematic view illustrating the glucose extraction principle used in the embodiment of the blood sugar measuring device of FIG. 1.
Figure 18:
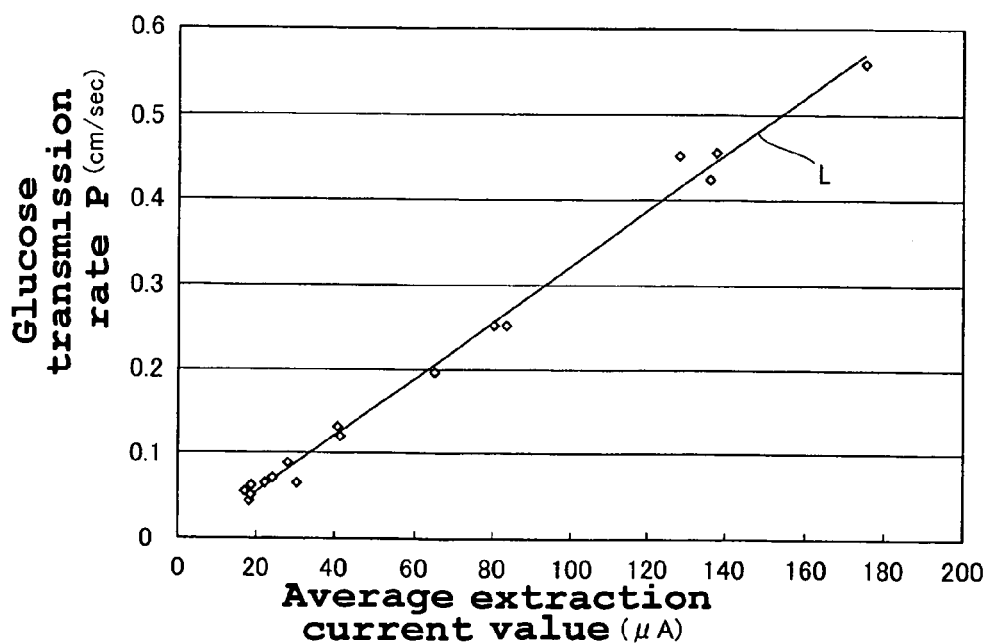
FIG. 18 is a distribution diagram showing the relationship between the average extraction current value and glucose transmission rate in glucose extraction.

FIG. 12 is a flow chart showing the sequence of the blood sugar measuring operation used in the embodiment of the blood sugar measuring device of FIG. 1. FIGS. 13 through 17 are schematic views illustrating the glucose extraction principle used in the embodiment of the blood sugar measuring device of FIG. 1. FIG. 18 is a distribution diagram showing the relationship between the average extraction current value and glucose transmission rate in glucose extraction. The sequence of the blood sugar level measuring operation of the embodiment of the blood sugar measuring device 100 of the present invention is described below with reference to FIGS. 1 through 3, FIG. 6, and FIGS. 9 through 18.

First, in step S1 in FIG. 12, the band 110 (refer to FIG. 1) is installed on the wrist 120 of the subject. At this time, the band 110 is installed so that the measurement location (extraction area) is positioned within the opening (not shown in the drawing) of the anchoring fixture of the band 110.

Figure 13:
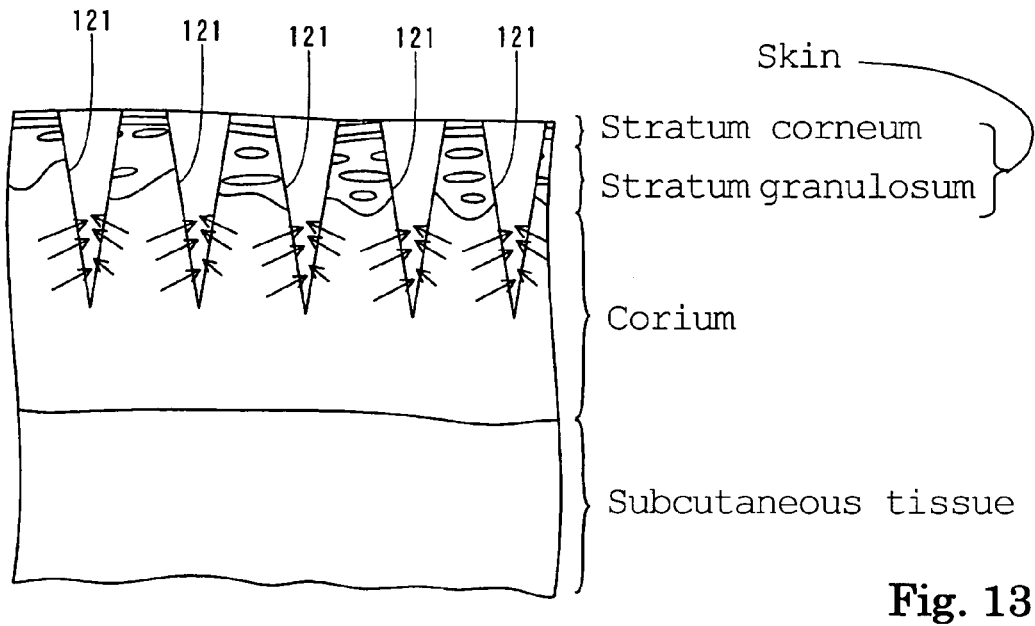
FIG. 13 is a schematic view illustrating the glucose extraction principle used in the embodiment of the blood sugar measuring device of FIG. 1.
Figure 14:
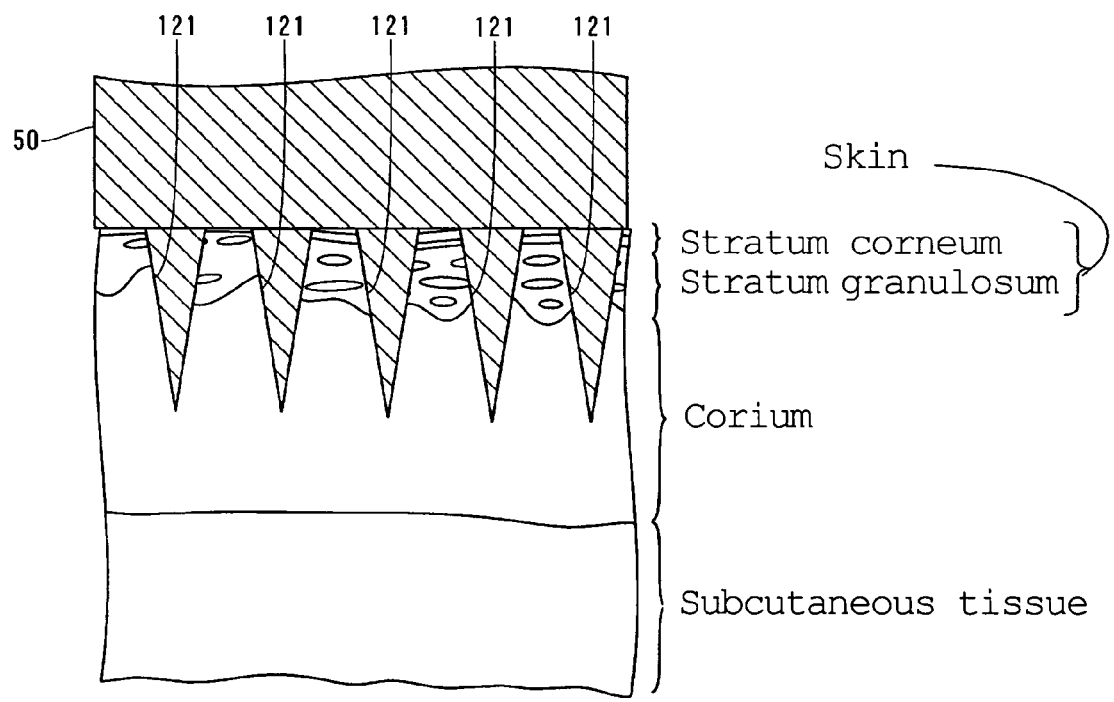
FIG. 14 is a schematic view illustrating the glucose extraction principle used in the embodiment of the blood sugar measuring device of FIG. 1.
Figure 15:
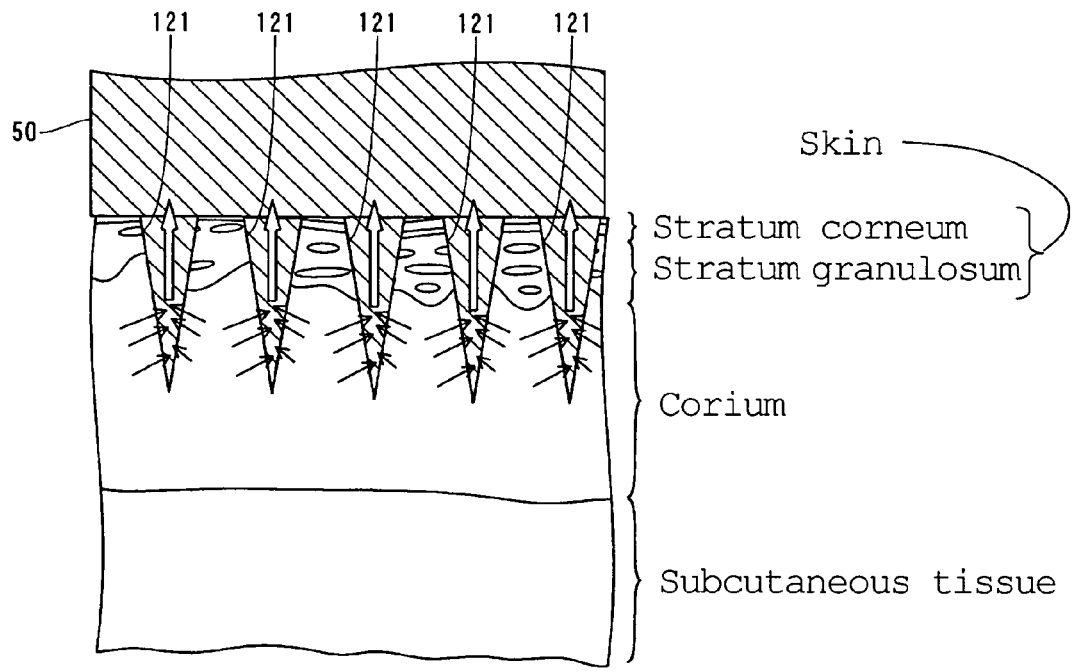
FIG. 15 is a schematic view illustrating the glucose extraction principle used in the embodiment of the blood sugar measuring device of FIG. 1.
Figure 16:
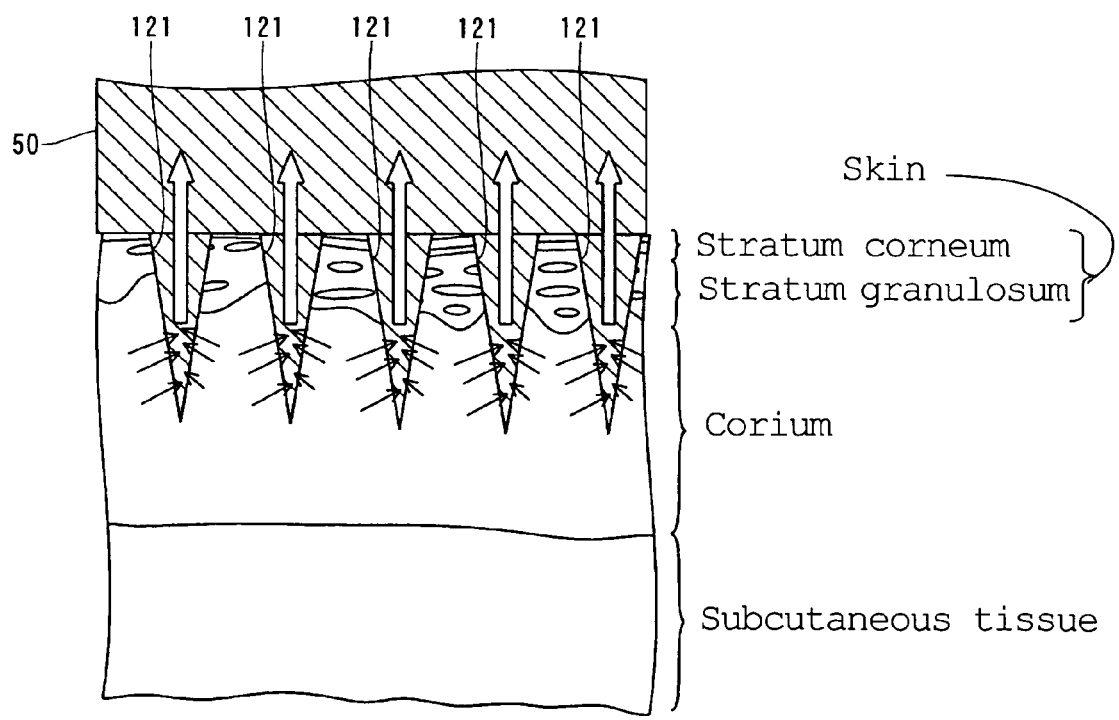
FIG. 16 is a schematic view illustrating the glucose extraction principle used in the embodiment of the blood sugar measuring device of FIG. 1.

In step S2 in FIG. 12, preprocessing is performed using the needle roller 130 (refer to FIG. 10). Specifically, a plurality of small extraction holes 121 are formed, as shown in FIG. 11, by pressing the needles 133 against the extraction area of the skin. Interstitial fluid containing glucose accumulated in the corium of the dermis is gradually extracted, as shown in FIG. 13, to the extraction holes 121 of the skin formed by the preprocessing using the needle roller 130.

In step S3 of FIG. 12, the blood sugar measuring device 10 is mounted on the anchoring fixture of the band 110. In this way the blood sugar measuring device 100 is installed on the wrist of the subject, as shown in FIG. 1. As shown in FIG. 6, the bottom surface of the extraction cartridge 20 comes into contact with the skin of the subject. At this time, the skin at the measurement location (extraction area) of the wrist 120 swells due to the tightening of the band 110 (refer to FIG. 1), such that the center part of the paper sheet 50 is moved upward so as to come into contact with the bottom surface (measuring surface 70a) of the sensor 70.

In step S4 of FIG. 12, the purified water accommodated in the syringe 13 is supplied through the tube 13a and purified water supply path 43 to the connection 50a of the paper sheet 50 of the extraction cartridge 20 when the measurement start switch 14 is pressed on the blood sugar measuring device 100, as shown in FIG. 2. In this way the paper sheet 50 becomes saturated with the purified water within a short time through capillary action.

At this time, the purified water contained in the paper sheet 50 enters the interior part of the extraction holes 121 formed in the skin. As indicated by the arrow in FIG. 15, the interstitial fluid within the extraction holes 121 is diffused throughout the purified water held by the paper sheet 50 when the interstitial fluid extracted to the extraction holes 121 mixes with the purified water from the paper sheet 50. In this way the interstitial fluid from the corium is again extracted to the extraction holes 121 since the osmotic pressure within the extraction holes 121 is lower than the osmotic pressure of the corium of the skin. As a result, interstitial fluid extracted through the extraction holes 121 formed in the skin is diffused to a certain degree in the purified water held by the paper sheet 50 before the voltage from the constant voltage power source 15 is applied to the positive electrode 60a and negative electrode 60b (refer to FIG. 6) of the extraction cartridge 20.

In step S5 of FIG. 12, a constant voltage of 0.5 V or more but less than 1.0 V from the constant voltage power source 15 shown in FIG. 6 is applied for approximately 3 minutes between the positive electrode 60a and negative electrode 60b. In this way the ion component carried by the charge in the extraction holes 121 positively migrates toward the positive electrode 60a and negative electrode 60b (refer to FIG. 6), as indicated by the arrows in FIG. 16. As a result, glucose in an amount detectable by the detection unit 30 (refer to FIG. 9) is harvested from the living tissue to the purified water held in the paper sheet 50 in conjunction with the migration of the ion component. At this time, the magnitude (current value) of the current flowing from the constant voltage power source 15 to the positive electrode 60a is measured by the ammeter 15a, and the measured current value is output to the control unit 11. The control unit 11 calculates the average value (average extraction current value) of the current values measured by the ammeter during the period (approximately 3 minutes) in which the constant voltage is applied by the constant voltage power source 15.

The mechanism by which glucose is extracted from living tissue is described below with reference to FIG. 17. When a voltage is applied by the constant voltage power supply 15 between the positive electrode 60a and negative electrode 60b, that is, when an electric field is generated in the living tissue by the constant voltage power source 15, the collector electrode 61a of the positive electrode 60a carries a positive (+) charge, and the collector electrode 61b of the negative electrode 60b carries a negative (−) charge. Activated carbon electrodes 62a and 62b, which are respectively adhered below the collector electrode 61a of the positive electrode 60a and the collector electrode 61b of the negative electrode 60b, are polarizable. Therefore, the bottom part within the activated carbon electrode 62a on the positive electrode 60a side is positively (+) charged, and the bottom part within the activated carbon electrode 61b on the negative electrode 60b side is negatively (−) charged. In this way the sodium ions (Na$^+$) and chloride ions (Cl$^-$) contained in the interstitial tissue extracted to the small extraction holes 121 formed in the skin by the preprocessing using the needle roller 130 (refer to FIG. 10) respectively migrate toward the activated carbon electrode 62b on the negative electrode 60b side and activated carbon electrode 62a on the positive electrode 60a side in the purified water of the paper sheet 50 under the influence of the electric field. The biochemical components such as glucose move into the collection medium (purified water absorbed in the paper sheet 50 in the present embodiment) in conjunction with the migration of the sodium ions (Na$^+$) and chloride ions (Cl$^-$) toward the activated carbon electrodes 62b and 62a. Then, the biochemical components such as glucose move within the purified water held by the paper sheet 50, and reach the measuring surface 70a of the sensor 70.

In step S6 of FIG. 12, the extraction speed (extracted amount per unit time) by which glucose was extracted to the purified water of the paper sheet 50 is calculated.

Specifically, the glucose that reaches the measuring surface 70a reacts with the catalyst glucose oxidase, and the hydrogen peroxide ($H_2O_2$) produced as a result then reacts with the catalyst peroxidase. As a result, active oxygen is produced. The color-producing agent painted on the measuring surface 70a reacts with and colors the active oxygen. Accordingly, the color-producing agent produces a strong color in accordance with the amount of glucose extracted from the living tissue.

The intensity of the light completely reflected within the second optical waveguide path 73 of the sensor 70 in contact with the paper sheet 50 (refer to FIG. 6) containing the purified water changes according to the intensity of the light of the color-producing agent, which corresponds to the amount of glucose extracted from the living tissue.

As a result, the light impinging the photoreceptor element has an intensity that corresponds to the amount of glucose that arrived at the measuring surface 70a, and a signal corresponding to that light intensity is output. Then, the control unit 11 calculates the amount of extracted glucose based on the signal output from the photoreceptor element 34. The control unit 11 calculates the glucose extraction speed by dividing the calculated amount of extracted glucose by the length of time (approximately 3 minutes) the voltage was applied by the constant voltage power source 15.

In step S7 of FIG. 12, the control unit 11 calculates the blood sugar level using the analysis method of equation (1) below based on the average extraction current value calculated in step S5 and the glucose extraction speed calculated in step S6. The value calculated by equation (1) below is the concentration of the glucose contained in the interstitial tissue the body, however, the calculation result of equation (1) is designated the blood sugar level in the present embodiment since the concentration of glucose contained in the interstitial tissue is substantially equal to the concentration of glucose contained in the Blood (blood sugar level).

$$BG = C/P \qquad (1)$$
$$= C/(A \times I + B)$$

In equation (1), BG represents the calculated blood sugar level, C represents the glucose extraction speed obtained using the sensor 70 in step S6, P represents the glucose transmission rate (easiness of glucose pass-through) at the extraction area, and I represents the average extraction current value measured by the ammeter 15a in step S5 and calculated by the control unit 11. Furthermore, A and B represent constants set beforehand. Equation (1) is stored in the control unit 11 beforehand, and is read from memory for the calculation of the blood sugar level each time the blood sugar level is measured. Thereafter, the calculated blood sugar level is displayed on the display unit 12 (refer to FIG. 1) together with the glucose extraction speed.

In step S8 of FIG. 11, the blood sugar measuring device 100 is removed from the anchor fixture of the band 110. Thereafter, in step S9, the band 110 is removed from the wrist 120 of the subject. Thus, blood sugar measurement using the blood sugar measuring device 100 is completed.

The constants A and B of equation (1) are determined in the manner described below. That is, a plurality of subjects who have blood sugar levels within the normal range use the blood sugar measuring device 100, and their glucose extraction speeds C and average extraction current values are acquired a plurality of times by repeatedly performing the previously described operations from step S1 through step S6 of FIG. 12. Then, the blood sugar levels D of the plurality of subjects who have blood sugar levels in the normal range are acquired several times by repeatedly performing the blood sugar measurement using a blood sugar measuring device other than the blood sugar measuring device 100 (for example, the Nipro Freestyle manufactured by Nipro Corporation).

Then, the glucose transmission rate P is calculated by equation (2) using the blood sugar levels D and the glucose extraction speeds C obtained as described above.

$$P=C/D \quad (2)$$

Then, as shown in FIG. 18, a plurality of data points (I, P) of the average extraction current value I and glucose transmission rate P are plotted on a coordinate system in which the average extraction current values I are set on the horizontal axis and the glucose transmission P rate are set on the vertical axis, to create a distribution diagram of the plurality of data (I, P). It can be understood from this distribution diagram that the average extraction current value I and glucose transmission rate P have a proportional correlation. Thereafter, the equation (P=A×I+B) represents the line L that describes the relationship between the average extraction current value I and glucose transmission rate P. The A and B of the equation (P=A×I+B) representing the line L then are designated the constants A and B of equation (1). Thus, the constants A and B of equation (1) are determined in this manner.

In the present embodiment, the analyte can be efficiently collected because the glucose moving toward the positive electrode 60*a* and negative electrode 60*b* is collected in the purified water absorbed and held by one sheet of paper 50 by providing in the extraction cartridge 20 the paper sheet 50 containing purified water to collect the glucose extracted from the living tissue such that the paper sheet 50 is in contact with the positive electrode 60*a* and negative electrode 60*b* connected to the constant voltage power source 15. That is, the purified water as collection medium for collecting the analyte extracted from living tissue is absorbed and held in the paper sheet 50 as absorbent member, and the paper sheet 50 is simultaneously brought into contact with the positive electrode 60*a* and negative electrode 60*b*, such that the positive electrode 60*a* and negative electrode 60*b* are maintained in a state of continuous connectedness by means of the purified water as collection medium. Thus, since the analyte moving toward the plurality of electrodes is collected in the collection medium, the analyte is efficiently collected as compared to when the analyte moving toward a plurality of electrodes is collected in a plurality of collection media corresponding to each electrode. Accordingly, the analyte can be extracted from the subject in an amount necessary for analysis within a predetermined time without a large current that may cause pain in the subject flowing to the living tissue.

In the present embodiment, the surface area of the glucose extraction area of the subject can be reduced by providing the single paper sheet 50, which contains purified water to collect the glucose extracted from the subject, in the extraction cartridge 20, as described above. In this way the burden placed on the subject by the preprocessing can be reduced since the surface area is reduced for the preprocessing of the extraction area.

By providing the single paper sheet 50 containing purified water to collect the glucose extracted from the living tissue, and the control unit 11 for analyzing the glucose extracted to the paper sheet 50 containing purified water in the present embodiment, information of the living tissue, such as blood sugar level and the like, can be measured directly since the glucose is extracted from the living tissue to the single paper sheet 50 containing purified water, and this glucose can be analyzed by the control unit 11. In this way the measurement of living tissue information, such as blood sugar level and the like, can be accomplished with higher accuracy unlike when the blood sugar level is measured directly using optical information obtained by irradiating a finger with light.

In the present embodiment, the current flowing within the living tissue is extremely small since analyte can be extracted from the living tissue without forming current paths circulating between the constant voltage power source 15 and within the living tissue by providing the constant voltage power source 15 for inducing an electric field in the living tissue through the paper sheet 50 that contains the nonconductive material of purified water, and providing the paper sheet 50 for collecting the analyte extracted from the living tissue in the presence of the electric field induced by the constant voltage power source 15. Accordingly, the pain felt by the subject is greatly reduced.

In the embodiment described above, a blood sugar level can be obtained without collecting blood from the subject by a construction in which the controller 11 calculates the blood sugar level BG based on the average extraction current I obtained by analyzing the current values measured by the ammeter 15*a*, and the glucose extraction speed obtained by analyzing the signals output from the detection unit 30.

Furthermore, purified water is used as the collection medium in the present embodiment. When a nonconductive material such as purified water is used, no current flows through the collection medium of nonconductive material between the first electrode and second electrode, therefore less energy can be applied by the power source to the electrodes compared to when a conductive material is used as the collection medium. When using a nonconductive material, such as purified water, that permits the ions extracted from living tissue to migrate within the collection medium, analyte extracted from the living tissue also moves within the collection medium in conjunction with the migration of the ions. In this way analyte extracted from living tissue can be easily collected even when the collection medium is a nonconductive material. A nonconductive gel may be used in place of a nonconductive fluid, such as purified water. When purified water is used, the collection medium is inexpensive. Furthermore, in this case the collection medium does not have adverse physical effects.

In the present embodiment, since purified water is used as a nonconductive collection medium and an absorbent member capable of absorbing and holding a fluid is provided, the collection medium is held in an absorbent member that allows easy handling of the collection medium. In this case, the use of paper or a mesh sheet as the absorbent member is desirable.

Accordingly, the absorbent member can be constructed inexpensively. When paper is used as the absorbent member, there is no concern that the absorbent member will have adverse physical effects.

In the present embodiment, at least one part of the first electrode and second electrode is formed of a material that has a specific surface area of 100 $m^2/g$ or more but less than 5000 $m^2/g$. According to this structure, less energy is applied from the power source to the electrodes since a sufficient current can be obtained by a voltage that is less than the electrode reaction potential. Thus, the pain felt by the subject can be minimized. When the specific surface area of the material is increased due to the complexity of the shape of the plurality of pores formed in the surface of the material, problems arising from the current reaching into the pores due to the excessive complexity of the pore shape can be suppressed by using material that has a specific surface area of less than 5000 $m^2/g$ for at least one part of the first electrode and second electrode. In this way it is possible to avoid an actual reduction in the specific surface area relative to the specific surface area logically possessed by the material.

In the present embodiment, the first electrode includes a positive electrode, and the holding unit holds the positive electrode, negative electrode, and collection medium. According to this structure, an easily handleable analyte extraction device is provided since the positive electrode, negative electrode, and collection medium are held in the holding unit. In this case, it is desirable that the positive electrode and negative electrode are arranged in the holding unit so as to be mutually opposed with a predetermined spacing therebetween.

In the present embodiment, the positive electrode and negative electrode are arranged in the holding unit so as to not come into contact with the skin when the collection medium comes into contact with the skin. According to this structure, since the positive electrode and negative electrode are arranged within the holding unit so as to not come into contact with the skin of the subject, pain felt by the subject is avoided even if a relatively large amount of energy is applied to the electrodes by the power source.

In the present embodiment, a collection medium storage unit is provided for storing the collection medium, and a flow path is further provided to move the collection medium from the collection medium storage unit to the holding unit, the flow path connecting the collection medium storage unit and the holding unit. According to this structure, since the collection medium is stored within the device sealed in the collection medium storage unit, it is possible to prevent deterioration of the collection medium and sensor in a relatively short time caused when the enzyme contained in the sensor comes into contact with the moisture of the collection medium, whether it be a fluid or gel, unlike the case wherein the collection medium is maintained in a state of contact with sensor used to detect the analyte. In this way the collection medium and the sensor used to detect the analyte can be preserved for a long time.

In the present embodiment, an absorbent member is used to absorb and hold the purified water collection medium, and the absorbent member is held in the holding unit. According to this structure, since the purified water and absorbent member are maintained separately within the device, it is possible to prevent deterioration of the collection medium and sensor in a relatively short time caused when the enzyme contained in the sensor comes into contact with the purified water, unlike the case wherein the purified water is maintained in a state of contact with sensor used to detect the analyte. In this way the purified water and the sensor used to detect the analyte can be preserved for a long time. Furthermore, the collection medium can be readily absorbed by the absorbent member when the analyte is extracted.

The present embodiment provides a device body that includes the power source and control unit of the extraction device, and provides an extraction cartridge that includes the first electrode and second electrode of the extraction device, and the holding unit of the extraction device, and is constructed so as to be removably installed in the device body. According to this structure, since the extraction cartridge is removable from the device body, the subject can simply repeat the replacement of the extraction cartridge to analyze the analyte. Furthermore, the detection unit includes a light source, an analyte sensor that is in contact with the collection medium when the extraction cartridge is installed in the device body and is irradiated with light from the light source, and an optical detector for detecting the irradiating light from the light source through the analyte sensor; the light source and optical detector are provided in the device body, and the analyte sensor is provided in the extraction cartridge. According to this structure, since the analyte sensor, which must be replaced for each measurement since it comes into contact with the analyte, is provided in the extraction cartridge, the analyte sensor can be easily replaced by simply removing the extraction cartridge from the device body.

In the present embodiment, the analyzer is further provided with a current value acquiring unit for acquiring the value of the current flowing from the power source of the extraction device to the first electrode of the extraction device, and the controller obtains the concentration of the components of the interstitial fluid in the living tissue of the subject based on the information obtained by the detection unit, and the current value obtained from the current value acquiring unit. According to this structure, the concentration of components in the interstitial fluid in the living tissue of the subject can be obtained without collecting blood from the subject. In this way, if, for example, the concentration of glucose contained in the interstitial fluid is obtained, it is possible to determine the blood sugar level of the subject without collecting blood.

In the present embodiment, by providing an electric field inducing means for inducing an electric field in living tissue through a nonconductive material, and providing a collection medium for collecting analyte extracted from living tissue in the presence of the electric field induced by the electric field inducing means, a very small current flows within the living tissue when extracting analyte from the living tissue without forming a current circuit circulating from the electric field inducing means and within the living tissue. Accordingly, the pain felt by the subject is greatly reduced. In the present embodiment, since at least one among the first electrode and second electrode includes a collector electrode connected to the power source, and a polarized electrode in contact with the collector electrode, ions within the living tissue can be easily collected in the collection medium through the polarity of the polarized electrode in contact with the collector electrode connected to the power source, such that analyte can be easily extracted from the living tissue in conjunction with the migration of the ions. In this case, the collector electrode is desirably formed of metal.

In the present embodiment, at least one among the first electrode and second electrode includes a member formed of activated carbon. Since the specific surface area of activated carbon is greater than the specific surface area of conventional electrodes, an adequate current can be obtained by a voltage that is less than the electrode reaction potential. Accordingly, analyte can be efficiently extracted using less energy generated by the power source. Thus, the pain felt by the subject can be minimized.

The present embodiment is to be considered an example in all aspects, and not in anyway limiting the present invention. The scope of the present invention is expressed in the scope of the claims and not in the description of the embodiment, and it is to be further noted that the embodiment may be variously modified insofar as such modifications fall within the equivalent meanings and scope of the claims.

For example, although the present embodiment describes an example wherein the present invention is applied to a blood sugar measuring device for measuring a blood sugar level by extracting glucose from living tissue and analyzing the extracted glucose, the present invention is not limited to this application inasmuch as the present invention is also applicable to glucose extraction devices that only extract glucose from living tissue. That is, the present invention is also applicable to a glucose extraction device, the structure of which omits the detection device from the blood sugar measuring device of the previously described embodiment. In this case, the user dispenses the glucose extracted to purified water from the glucose extraction device to another analyzer, and thereafter analyzes the glucose and calculates the blood sugar level in the other analyzer.

Although the present embodiment has been described by way of example of applying glucose oxidase as an enzyme for reacting with glucose, the present invention is not limited to this example, inasmuch as enzymes other than glucose oxidase, such as pyranose oxidase, hexokinase, glucokinase, glucose dehydrogenase, as enzymes reacting with glucose.

Although the present embodiment has been described by way of example wherein an activated carbon electrode configured by activated carbon having a specific surface area of approximately 1000 $m^2/g$ to approximately 3000 $m^2/g$ is adhered to a collector electrode formed of aluminum, the present invention is not limited to this example inasmuch as an electrode formed of foamed carbon having a specific surface area of approximately 500 $m^2/g$ to approximately 800 $m^2/g$ by a cellulose derivative, and doped polymer (polyaniline) having a specific surface area of approximately 200 $m^2/q$ to approximately 400 $m^2/g$ as a porous conductive material may also be adhered to a collector electrode formed of aluminum. Furthermore, an electrode formed of silver (Ag) and silver chloride (AgCl) may be adhered to a collector electrode without using a porous conductive material such as activated carbon.

Although the present embodiment uses an optical sensor as the sensor for detecting glucose, the present invention is not limited to this example inasmuch as an electrical sensor, such as a sensor-electrode assembly, such as that disclosed in International Patent Publication No. 96/00110 or the like, may be used as a sensor for detecting glucose.

Although the present embodiment describes an example wherein the sensor is incorporated in the extraction cartridge, the present invention is not limited to this example inasmuch as the sensor may be mounted on the device body (analysis unit) separate from the extraction cartridge.

Although the present embodiment describes an example using a sheet of paper as the absorbent member, the present invention is not limited to this example inasmuch as a nylon sheet (mesh sheet) having a reticulate structure other than a sheet of paper, and a nonsheet-like paper or nylon may also be used as the absorbent member. Furthermore, a nonconductive gel, such as polyacrylate and the like, may also be used as a collection medium adhered to a plate-like member. A conductive collection medium, such as sodium chloride aqueous solution and the like, may also be used in place of the nonconductive collection medium. When a conductive collection medium is used, the current flowing within the receiving chamber (holding unit) that does not participate in the glucose extraction is increased. Thus, a nonconductive collection medium is desirable since analyte extraction can be accomplished using a smaller current. A sheet-like absorbent member is desirable from the perspective of getting close the skin and electrodes. The analyte extraction speed can be increased by getting close to the skin and electrodes.

Figure 19:
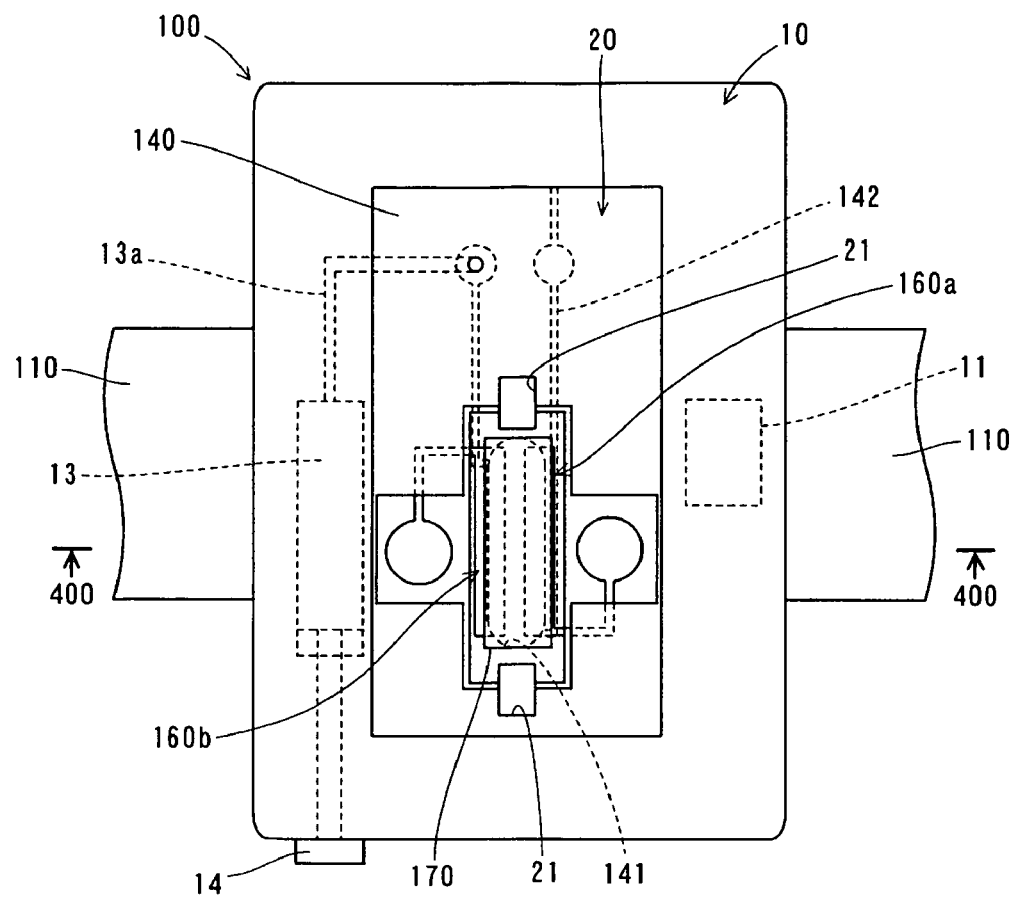
FIG. 19 is a top view showing the internal structure of a modification of the blood sugar measuring device of the present invention.
Figure 20:
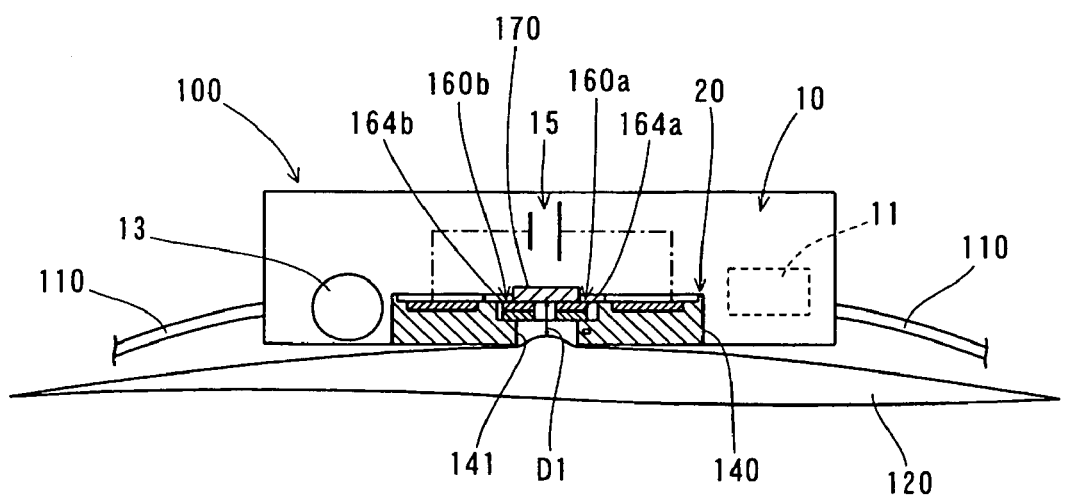
FIG. 20 is a section view on the 400-400 line of FIG. 13.

A modification of the previously described embodiment of the present invention is shown in FIGS. 19 and 20, wherein the paper sheet 50 is omitted, and purified water is supplied directly into the main body opening 42. In this modification, the region formed by a sensor 170, positive electrode 160a and negative electrode 160b, and the opening 141 provided on the cartridge body 140 function as a receiving chamber (holding unit) to maintain the purified water. Furthermore, a discharge path 142 connected to the outside of the device is provided in the receiving chamber (holding unit), as shown in FIG. 19. The purified water used as a collection medium in this modification of the embodiment is held within the receiving chamber (holding unit) as one continuous body. In this modification, when the blood sugar measuring device 100 is installed on the wrist 120 of the subject, the distance D1 (refer to FIG. 20) between the skin of the wrist 120 of the subject and the bottom surface of the sensor 170 is set to approximately 0.3 mm to approximately 1 mm. When the distance D1 is set less than 0.3 mm, the subject may feel greater pain since there is a possibility that the positive electrode 160a or negative electrode 160b might come into contact with the skin of the wrist 120 of the subject. Therefore, the distance D1 is desirably set at 0.3 mm or more.

Figure 21:
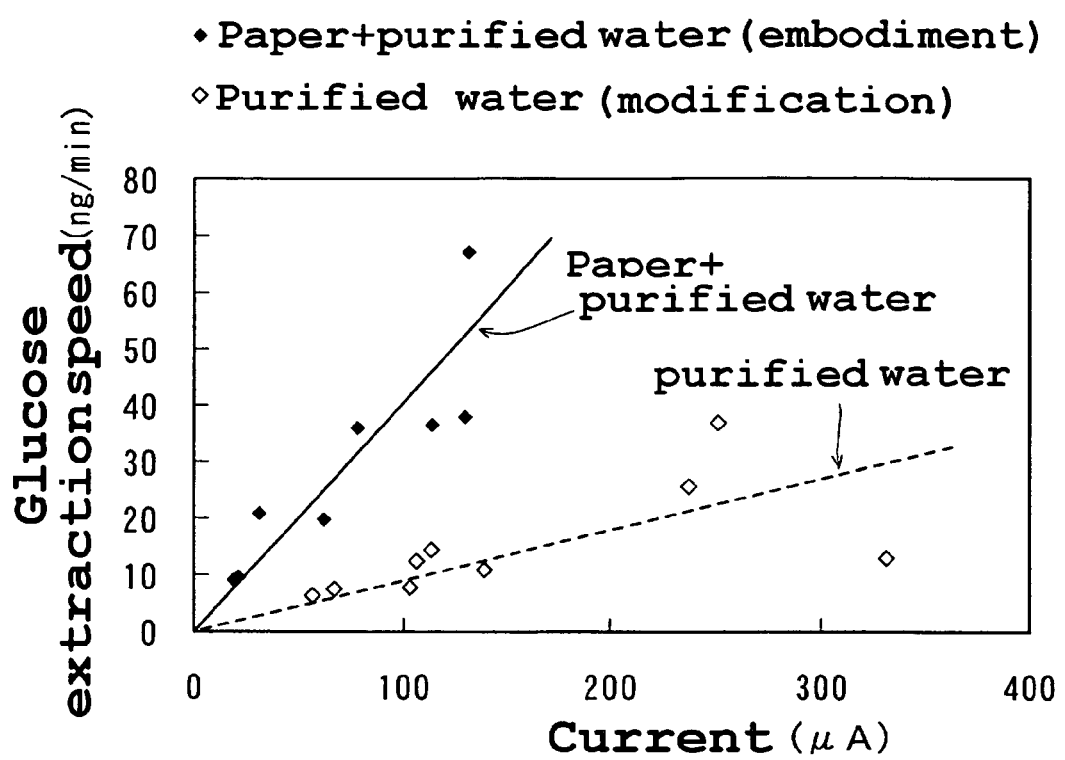
FIG. 21 shows the relationship between electrical current and glucose extraction rate when paper containing purified water is used as the collection medium, and when only purified water is used as the collection medium.

When purified water and a paper sheet 50 are respectively used as the glucose collection medium and absorbent member for the collection medium as in the embodiment of the present invention (refer to FIGS. 2 and 3), the glucose extraction speed increases relative to the magnitude of the current flowing to the positive electrode and negative electrode compared to when the paper sheet 50 is omitted as in the modification of the embodiment of the present invention (refer to FIGS. 19 and 20), as shown in FIG. 21. This increase is thought to occur because the distance (approximately 0.15 mm) between the skin of the wrist 120 of the subject and the bottom surface of the sensor 70 in the embodiment of the present invention is quite small compared to the distance (approximately 0.3 to approximately 1 mm) between the skin of the wrist 120 of the subject and the bottom surface of the sensor 170 in the modification of the embodiment of the present invention. In this way when purified water and a paper sheet 50 are respectively used as the glucose collection medium and absorbent member for the collection medium, the subject feels less pain because a predetermined amount of glucose can be extracted by a small current. Therefore, it is desirable that purified water and a paper sheet 50 are respectively used as the glucose collection medium and absorbent member for the collection medium as in the embodiment of the present invention.

Although the present embodiment provides an example wherein purified water is supplied to the paper sheet of the extraction cartridge from the syringe of the analysis unit before the measurement, the present invention is not limited to this example inasmuch as the purified water and paper sheet may be maintained beforehand within the extraction cartridge in a state of noncontact by means of a separating member, such that the purified water may be supplied to the paper sheet by removing a separating member directly prior to measurement.

Although the above embodiment is described by way of example wherein a voltage is applied to the positive electrode and negative electrode using a direct current type constant voltage power source, the present invention is not limited to this example inasmuch as a voltage also may be supplied to the positive electrode and negative electrode using an alternating current type constant voltage power source.

Although the present embodiment has been described by way of example wherein preprocessing is performed using a needle roller on the skin of the subject before measuring the blood sugar level using the blood sugar measuring device, the present invention is not limited to this example inasmuch as the blood sugar level may be measured using the blood sugar measuring device without preprocessing the skin of the subject using the needle roller. Preprocessing of the skin of the subject using the needle roller is desirable when measuring the blood sugar level using the blood sugar measuring device since such preprocessing increases and stabilizes the amount of extracted analyte. Furthermore, preprocessing using the needle roller is also desirable because the analyte can be extracted at a low voltage, thereby reducing the pain felt by the subject.

Although the present embodiment has been described by way of example wherein the present invention is applied to a blood sugar measuring device for extracting glucose and calculating a blood sugar level, the present invention is not limited to this example inasmuch as the present invention is also applicable to an extraction device for extracting an analyte other than glucose from living tissue. The analyte extracted by the extraction device to which the present invention is applicable may be, for example, a biochemical component, drug administered to the subject and the like. Examples of proteins, which are one type of biochemical component, include albumin, globulin, enzymes and the like. Examples of biochemical components other than proteins include creatinine, creatine, uric acid, amino acids, fructose, galactose, pentose, glycogen, lactic acid, pyruvic acid, ketones and the like. Examples of drugs include manufactured digitalis, theophylline, arrhythmia medication, epilepsy medication, aminoglycoside antibiotics, glycopeptide antibiotics, antithrombotic medication, immunosuppressants and the like.

In the blood sugar level measuring device of the above embodiment, or when the present invention is applied to an extraction device for extracting analyte other than glucose from living tissue, the detection unit and control unit may be configured so as to analyze proteins or biochemical components and drugs other than proteins using measurement methods other than the method used in the above embodiment, such as high performance liquid chromatography (HPLC).

Although the result of the calculation of equation (1) is used as the blood sugar level in the present embodiment, the present invention is not limited to this example inasmuch as the blood sugar level also may be calculated using a predetermined equation other than equation (1).

What is claimed is:

1. A device for extracting glucose from living tissue of a subject, the device comprising:
   an extraction cartridge removably installed in the device; and
   a main body;
   wherein the extraction cartridge comprises:
      an absorbing member for holding purified water for collecting the glucose extracted from the living tissue;
      a chamber for holding the absorbing member;
      a purified water supply path for supplying the purified water to the absorbing member;
      a first and second electrode, the first electrode disposed adjacent the absorbing member in the chamber and the second electrode disposed on an opposite side of the absorbing member in the chamber from the first electrode; and
      a mounting part; and
   wherein the main body comprises:
      a power source for applying a voltage for moving the glucose to the purified water using the electrodes;
      a pump for holding and supplying the purified water to the absorbing member through the purified water supply path; and
      a connection part for engaging the mounting part.

2. The device of claim 1, wherein the absorbing member comprises paper or a mesh sheet.

3. The device of claim 1, wherein the chamber comprises an opening for contacting the absorbing member with skin of the subject.

4. The device of claim 1, wherein the extraction cartridge further comprises an end terminal for connecting to the power source.

* * * * *

UNITED STATES PATENT AND TRADEMARK OFFICE
CERTIFICATE OF CORRECTION

| | | |
|---|---|---|
| PATENT NO. | : 8,046,043 B2 | Page 1 of 1 |
| APPLICATION NO. | : 11/280100 | |
| DATED | : October 25, 2011 | |
| INVENTOR(S) | : Asano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 647 days.

Signed and Sealed this
Thirteenth Day of March, 2012

David J. Kappos
*Director of the United States Patent and Trademark Office*